United States Patent
Tang et al.

(10) Patent No.: US 10,078,056 B2
(45) Date of Patent: Sep. 18, 2018

(54) X-RAY PRODUCT QUALITY ONLINE INSPECTION DEVICE

(71) Applicant: Nuctech Company Limited, Beijing (CN)

(72) Inventors: Huaping Tang, Beijing (CN); Zhiqiang Chen, Beijing (CN); Yuanjing Li, Beijing (CN); Zhuoyan Liu, Beijing (CN); Yonggang Wang, Beijing (CN); Zhanfeng Qin, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 0 days.

(21) Appl. No.: 14/901,970

(22) PCT Filed: Aug. 27, 2015

(86) PCT No.: PCT/CN2015/088257
§ 371 (c)(1),
(2) Date: Dec. 29, 2015

(87) PCT Pub. No.: WO2016/034072
PCT Pub. Date: Mar. 10, 2016

(65) Prior Publication Data
US 2016/0223473 A1 Aug. 4, 2016

(30) Foreign Application Priority Data
Sep. 2, 2014 (CN) .......................... 2014 1 0442118

(51) Int. Cl.
*A61B 6/03* (2006.01)
*G01N 23/04* (2018.01)
*B07C 5/34* (2006.01)

(52) U.S. Cl.
CPC ........... *G01N 23/04* (2013.01); *B07C 5/3416* (2013.01); *B07C 2501/0009* (2013.01)

(58) Field of Classification Search
CPC ................. H01J 35/08; H01J 2235/086; H01J 2235/087; H01J 35/14; G01N 5/0008; G01N 2223/64
(Continued)

(56) References Cited

U.S. PATENT DOCUMENTS 3,768,645 A    10/1973   Conway et al.
9,086,497 B2 *   7/2015   Bendahan .............. G01V 5/005
(Continued)

FOREIGN PATENT DOCUMENTS

CN    101907580 A    12/2010
CN    102313752 A     1/2012
(Continued)

OTHER PUBLICATIONS

Office Action dated Nov. 1, 2016, in Japanese Application No. 2016-546140 (4 pgs), and English-language translation of same (6 pgs); 10 pgs total.
(Continued)

*Primary Examiner* — Don Wong
(74) *Attorney, Agent, or Firm* — Knobbe Martens Olson and Bear LLP

(57) ABSTRACT

An X-ray product quality online inspection device of the present invention comprises: a distributed X-ray source having a plurality of targets and being able to generate X-rays for irradiating an inspected product from the plurality of targets in a predetermined sequence; a detector for receiving the X-rays generated by the distributed X-ray source and outputting a signal representing characteristics of the received X-rays; a transport device which is located between the distributed X-ray source and the detector for carrying the inspected product to pass through an X-ray radiation region, wherein the transport device is arranged as a continuous transport mechanism which matches a produc-
(Continued)

tion line of the inspected product; and a power supply and control device, which is used to supply power to and control the X-ray product quality online inspection device.

20 Claims, 3 Drawing Sheets

(58) Field of Classification Search
USPC .................................................. 378/57, 124
See application file for complete search history.

(56) References Cited

U.S. PATENT DOCUMENTS

| | | | |
|---|---|---|---|
| 2005/0067570 | A1 | 3/2005 | Retterath et al. |
| 2008/0037707 | A1 | 2/2008 | Rothschild et al. |
| 2010/0284509 | A1* | 11/2010 | Oreper ................. G01V 5/0041 378/5 |
| 2010/0310043 | A1 | 12/2010 | Shimada |
| 2011/0206179 | A1* | 8/2011 | Bendahan ............ G01V 5/0016 378/19 |
| 2011/0286581 | A1 | 11/2011 | Sprenger et al. |
| 2013/0270447 | A1 | 10/2013 | Krohmal |
| 2014/0185754 | A1 | 7/2014 | Tang et al. |
| 2014/0249663 | A1 | 9/2014 | Voillaume |
| 2014/0297228 | A1 | 10/2014 | Radley et al. |
| 2015/0014526 | A1* | 1/2015 | Bendahan ................. G01T 3/00 250/307 |

FOREIGN PATENT DOCUMENTS

| | | |
|---|---|---|
| CN | 103157607 A | 6/2013 |
| CN | 103901057 A | 7/2014 |
| CN | 103930772 A | 7/2014 |
| CN | 204359711 U | 5/2015 |
| CN | 204359712 U | 5/2015 |
| JP | 2010-0181424 A | 8/2010 |
| JP | 2011-017694 A | 1/2011 |
| JP | 2011-196837 A | 10/2011 |
| JP | 2014-521964 | 8/2014 |
| WO | WO 2013/057115 | 4/2013 |

OTHER PUBLICATIONS

Extended European Search Report dated Jun. 30, 2017, received in European Application No. 15804298.6, 6 pages.
First Office Action and Search Report dated Oct. 10, 2017, received in Chinese Application No. 201410442118.X (9 pgs), and concise English explanation thereof (2 pgs); 11 pages total.
Yao, Fulai et al., "Automation Equipment and Engineering Design, Installation, Commissioning, and Troubleshooting" ( ISBN 978-7-111-40227-5; CPEL1452979N); section 3.14 Vision Sensor, p. 34, dated Oct. 2012 (1st published Jan. 2013) retrieved from http://img.duxiu.com/n/print.isp on Sep. 7, 2017 (2 pgs), and concise English language explanation thereof (1 pg); 3 pages total.

* cited by examiner

X-RAY PRODUCT QUALITY ONLINE INSPECTION DEVICE

CROSS-REFERENCE TO RELATED APPLICATIONS

This application claims priority to PCT Application No. PCT/CN2015/088257, filed Aug. 27, 2015, published as WO/2016/034072, entitled "X-Ray Product Quality Online Inspection Device" and Chinese Patent Application No. 201410442118.X, filed on Sep. 2, 2014, published as CN105445290, which are hereby incorporated by reference in their entirety.

FIELD OF THE INVENTION

The present invention relates to a device for performing quality inspection on factory line products by use of X-ray, particularly relating to a device for performing a three-dimensional imaging inspection on products on production line by use of a distributed X-ray source.

BACKGROUND

X-ray sources are widely used in fields of industrial nondestructive testing, security check, medical diagnosis and treatment, etc. It is possible to analyze a fine structure of an object by transmission imaging of the object using a high penetration capability of X-rays. Thus, the purposes of structural analysis, defect inspection, effect verification, etc., for example, production quality inspection of the products on production line, can be achieved. Traditional X-ray source has only one target, that is, generating the X-rays from only one position. A new type of X-ray source, known as distributed X-ray source can generate X-rays from different positions.

Further, the X-ray sources have been applied to perform on-line inspection to industrial products on factory lines, such as electronic components, circuit boards, mechanical parts, metal cans, lithium ion batteries, glass bottles, metal defects and the like.

Patent Document 1 and the like use a traditional X-ray source with single target, and usually can achieve transmission imaging of the products on production lines in only one direction. Patent Document 2 and the like rotate an inspected product by 360 degree via an auxiliary device and continuously image the inspected product during the rotation, and thus achieving an "all-round" inspection. Patent Document 3 and the like perform multiple transmission imaging on a same product when it is located at different positions, and obtain a three-dimensional image by using "an iterative reconstruction algorithm of translation-type cone-beam CT based on sub-region equalization and total variation minimization". Patent Document 4 and the like use a plurality of X-ray sources to perform transmission imaging on the inspected products from different angles.

Patent Document 1: CN103698346A;
Patent Document 2: CN103644935A;
Patent Document 3: CN102590248A; and
Patent Document 4: CN202814895U.

SUMMARY OF THE INVENTION

An aspect of the present application provides an X-ray product quality automatic inspection device, which uses a distributed X-ray source to perform a multiple-angle quick imaging on a product, thereby obtaining a multi-view image or a three-dimensional image of the inspected product. Further, it is possible to automatically perform an all-round quality analysis on the product through a software system, and to execute a sorting according to the analysis result.

An aspect of the present application provides an X-ray product quality online inspection device, which comprises:

a distributed X-ray source having a plurality of targets, wherein the distributed X-ray source is able to generate X-rays for irradiating an inspected product, from the plurality of targets in a predetermined sequence;

a detector for receiving the X-rays generated by the distributed X-ray source and outputting a signal representing characteristics of the received X-rays;

a transport device which is located between the distributed X-ray source and the detector for carrying the inspected product to pass through an X-ray radiation region, wherein the transport device is arranged as a continuous transport mechanism which matches a production line for the inspected product; and a power supply and control device, which is used to supply power to and control the X-ray product quality online inspection device.

Further, in the X-ray product quality online inspection device of the present application, the power supply and control means further forms characteristic information of the inspected product according to the signal from the detector, and provides an inspection and analysis result of the inspected product according to the characteristic information.

Further, the X-ray product quality online inspection device of the present application further comprises a sorting device, which is located downstream of the distributed X-ray source and the detector in a moving direction of the inspected product, and is used to sort the inspected product according to the signal from the detector or the inspection and analysis result from the power supply and control device, under the control of the power supply and control device.

Further, in the X-ray product quality online inspection device of the present application, the power supply and control device determines whether the signal from the detector falls within a predetermined threshold range, and the sorting device sorts out the inspected product when it is determined that the signal from the detector does not fall within the threshold range.

Further, in the X-ray product quality online inspection device of the present application, the sorting device sorts out the inspected product in a case where the inspection and analysis result from the power supply and control device indicates that the characteristic information of the inspected product is inconsistent with standard characteristic information.

Further, in the X-ray product quality online inspection device of the present application, the power supply and control device further comprises an image construction subsystem, which is used to receive the signal from the detector and form a multi-view image or a three-dimensional image expressing the characteristic information of the inspected product.

Further, in the X-ray product quality online inspection device of the present application, the power supply and control device further comprises an image analysis subsystem, which is used to compare and analyze the inspected image obtained by the image construction subsystem and an image of a standard product according to a predetermined rule, and the inspected product is sorted according to the comparison and analysis result of the image analysis subsystem.

Further, in the X-ray product quality online inspection device of the present application, the power supply and control device further comprises a display and operation subsystem for displaying at least one of: operating state of the X-ray product quality online inspection device, an inspection image of the inspected product, the inspection and analysis result, and inputting of control instructions.

Further, in the X-ray product quality online inspection device of the present application, further comprises a shielding device, which encloses the X-ray radiation region and shields stray X-rays.

Further, in the X-ray product quality online inspection device of the present application, all the inspected products produced on the production line per unit time can be carried by the transport device to continuously pass through the X-ray product quality online inspection device within a unit time to finish the inspection.

Further, in the X-ray product quality online inspection device of the present application, the transport device itself is a part of a factory production line.

Further, in the X-ray product quality online inspection device of the present application, the plurality of targets of the distributed X-ray source are arranged in straight line, polyline, arc or the combination thereof.

Further, in the X-ray product quality online inspection device of the present application, an arrangement direction of the plurality of targets of the distributed X-ray source is perpendicular to the moving direction of the inspected product, or the plurality of targets of the distributed X-ray source are arranged in an arc shape or a spiral shape along the moving direction of the inspected product.

Further, in the X-ray product quality online inspection device of the present application, the detector is a flat panel detector having numerous detection units or a detector having a plurality of detection units in a one-dimensional linear array or a two-dimensional matrix array, and is able to receive the X-rays at a plurality of positions at the same time.

Further, in the X-ray product quality online inspection device of the present application, a sum of a field angle of the X-rays from the distributed X-ray source to any point on the inspected product and a field angle of the X-rays from the point to the detector is more than 180 degrees.

Further, in the X-ray product quality online inspection device of the present application, the distributed X-ray source is a dual-energy X-ray source and/or the detector is a dual-energy detector.

As described above, an aspect of the present application provides an X-ray product quality online inspection device comprising a distributed X-ray source, a detector, a transport device, a power supply and control device, a sorting device, etc. The X-ray product quality online inspection device can generate X-rays from a plurality of targets at different positions through the distributed X-ray source, and also matches the distributed X-ray source with the detector array. Thus, the inspected product on the factory production line can be transmitted and imaged from multiple views, a multi-view image or three-dimensional image can be obtained, and an all-round inspection and analysis on the products can be achieved. The operating states of the plurality of targets within the distributed X-ray source can achieve fast switch of electrical control at the level of microsecond, enabling a high inspection speed and a high efficiency. Further, the power supply and control device is provided with an image analysis subsystem, which compares and analyzes the inspected product image and a pre-stored standard product image according to predetermined rules. Thus, the automatic analysis on the inspection result of the products on the production line can be achieved, with a high efficiency and saved labors. Furthermore, the power supply and control device controls the sorting device to perform corresponding actions according to the result of the automatic analysis, and thus automatic sorting of the products can be achieved on the production line, with a high efficiency and saved labors.

The X-ray product quality online inspection device according to the present application can achieve an all-round inspection on the products on the factory line, can automatically analyze the inspection images, and can automatically sort the products on the production line according to the analysis result. The X-ray product quality automatic inspection device according to the present application can operate flexibly, has a strong adaptability for different products, can inspect products roundly and exhaustively, and has a high degree of automation. Thus, the present invention can significantly increase production efficiency and reduce production costs.

DETAILED DESCRIPTION

By studying and analyzing the Patent Documents 1-4, the inventor of the present application finds the following problems. Patent Document 1 can only obtain a plane image of inspected product. The image misses depth information in the X-ray radiation direction, and thus the inspection is not an "all-round" inspection and the inspection effect is limited. The inspection speed in Patent Document 2 is low due to the need for locating, rotating and continuously imaging of each product, and is difficult to match the production speed requirement of production lines. In Patent Document 3, since the effective view range of the products with respective to the X-ray source and the detector during the movement of products is limited, the quality of obtained image has a poor three-dimensional effect and the efficiency is low. In Patent Document 4, although the "all-round" inspection is achieved, the amount of views is small and the effect of the "all-round" inspection is limited if the number of the X-ray sources is small. If the number of the X-ray sources is increased, the image quality can be improved while the costs will be multiplied.

In contrast, an X-ray product quality inspection device according to one aspect of the present application can obtain multi-view image or three-dimensional image. Moreover, an X-ray product quality inspection device according to one aspect of the present application also can obtain image of high quality. Furthermore, an X-ray product quality inspection device according to one aspect of the present application also can have high inspection efficiency and match the production speed requirement of production lines.

In the following description, the present invention will be described in detail by reference to the accompany drawings.

Figure 1:
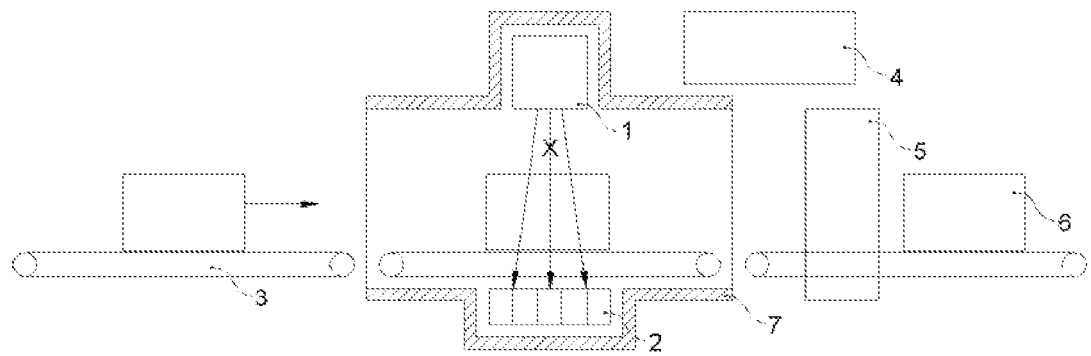
FIG. 1 shows a structural schematic diagram of an X-ray product quality automatic inspection device according to some embodiments of the present invention.

FIG. 1 shows a structural schematic diagram of an X-ray product quality automatic inspection device according to some embodiments of the present invention. As shown in FIG. 1, the X-ray product quality automatic inspection device according to the present invention includes an X-ray source 1, a detector 2, a transport device 3, and a power supply and control device 4. The X-ray source 1 is a distributed X-ray source that has a plurality of targets, and can generate X-rays from multiple positions. The detector 2 is used to receive the X-rays generated by the X-ray source, and to output signals representing the characteristics of the X-rays. The transport device 3 is located between the X-ray source 1 and the detector 2, for carrying an inspected product 6 to pass through an X-ray radiation region (that is, a region that is irradiated by the X-rays from the X-ray source 1). However, the transport device 3 is not limited to the above way, and can be embodied in other ways as long as it can make the inspected product 6 pass through the X-ray radiation region. The power supply and control device 4 can generate characteristic information of the inspected product 6 according to the signal from the detector 2. The type of the characteristic information can be, for example, of images, threshold ranges, gas or liquid, etc. Specifically, the power supply and control device 4 may include a power source subsystem 41 which supplies power to the X-ray source 1, the detector 2, etc. of the X-ray product quality inspection device, a control subsystem 42 which performs logic control to various parts of the X-ray product quality inspection device and enables a normal operation of the system, and an image construction subsystem 43 which receives the signal outputted from the detector 2 and forms an image reflecting the characteristics of the inspected product 6 (that is, the image expresses the characteristic information of the inspected product) via process of internal electronic circuit processing, software algorithm analysis and image reconstruction, etc. However, the structure of the power supply and control device 4 is not limited to this, and can be embodied as other structure as long as it can achieve the above-described functions. In the present invention, the power supply and control device 4 may include a characteristic analysis module, which can give out an inspection and analysis result of the inspected product according to the obtained characteristic information of the inspected product.

Furthermore, the X-ray source 1 is a distributed X-ray source which has a plurality of targets and can generate X-rays from a plurality of positions. The timings by which each target generates the X-ray can be flexibly controlled. The arrangement of the targets in the X-ray source may be of straight line, polyline, arc, the combinations thereof, etc. The targets are arranged in such a direction as to surround (or surround in a certain angular range) the inspected product. The arrangement direction of the plurality of targets in the X-ray source may be perpendicular to a moving direction of the inspected product. Furthermore, it is also possible to arrange the plurality of targets in an arc shape or a spiral shape along the moving direction of the inspected product 6. In this application, the arrangement of the plurality of targets in the X-ray source 1 is not particularly limited.

Further, the detector 2 is a linear detector array constituted by a plurality of detection elements, and the linear detector array includes one-dimensional linear array and two-dimensional matrix array. The arrangement of the detector array corresponds to that of the targets of the X-ray source, and the detector array is configured to surround the inspected product 6. Two-dimensional transmission image(s) of one slice or more than 2 slices of the inspected product 6 can be generated according to the information obtained by the detector 2 each time when each target generates X-ray. Further, the detector 2 may be a flat panel detector having a plurality of detection units, and two-dimensional transmission images of the inspected product 6 can be generated according to the information obtained by the detector 2 each time when each target generates X-ray. When the detector 2 is a flat panel detector, a higher image resolution can be obtained. However, the present invention is not limited to this, and any other detector may be applied to the X-ray product quality inspection device of the present invention, as long as it can receive the X-ray from the distributed X-ray source and convert the received X-ray into the signal for generating the image of the inspected product. Further, in the case where the detector 2 is in an array configuration, the arrangement of the detector array is not limited to be parallel to the X-ray source 1, and also may be perpendicular to the X-ray source 1 or correspond to the X-ray source 1 in any angle. Further, in the case where the detector array is perpendicular to the X-ray source 1, it is preferable that the detector array is in a shape of arc, the center of which is any one of the targets.

Further, as shown in FIG. 1, the transport device 3 is located between the X-ray source 1 and the detector 2, for carrying the inspected product 6 to pass through the X-ray radiation region. The transport device 3 may be an independent transporting segment which is controlled by the X-ray product quality inspection device, and is configured as a continuous transport mechanism which matches with the production line of the inspected product 6 and is arranged between standard production lines of a factory. The inspected product 6 is transported (unloaded) to the transport device 3 from an upstream standard production line, and the transport device 3 carries the inspected product 6 to pass through the X-ray radiation region and then transports (loads) the inspected product 6 to a downstream standard production line. Further, the transport device 3 also may be a part of the standard production line of the factory. Of course, the transport device 3 also may be at the end of the standard production line, so that the inspected product 6 is detected before leaving the line.

Further, the image construction subsystem 43 receives the signals outputted from the detector 2 and forms images reflecting the characteristics of the inspected product 6 via various processes, such as internal electronic circuit processing, software algorithm analysis, image reconstruction, etc. X-rays generated by each target of the X-ray source 1 penetrate through the inspected product 6 and are received by the array of the detector 2. The image construction subsystem 43 can form a transmission image of the inspected product 6 along a slice direction within a certain slice thickness, according to the signal outputted from the detector 2. The slice thickness is related to number of rows in the array of the detector 2. That is, the more rows the detector 2 has, the thicker the slice generated by each imaging is. After the targets at different positions of the X-ray source 1 generate X-rays sequentially and quickly (the time period during which each target emits X-rays may be at the level of microsecond, for example, 100 μs), it is possible to obtain multiple transmission images in different directions for the same slice (since the time period during which all the targets sequentially emit the X-rays is at the level of microsecond, for example, a total of 1 ms for 10 targets; and the distance moved across by the inspected product 6 during this time period is very small and the transmission images can be regarded as belonging to the same slice). These transmission images can form a two-dimensional slice image containing detailed information of the slice by image reconstruction. A series of slice images of the inspected product 6 are formed as the inspected product 6 continuously moves forward when it is carried by the transport device 3. The image construction subsystem 43 superimposes the series of slice images and forms a complete three-dimensional image of the inspected product 6.

During the above-mentioned process, each row in the detector array corresponds to a transverse slice. The more rows the detector array has, the larger the number of the slices obtained is when the targets of the X-ray source 1 generate X-rays each time, the larger the inspected thickness is, the faster the moving speed of the inspected product 6 carried by the transport device 3 is, and thus the faster the inspecting speed of the X-ray product quality inspection device is. When the detector 2 is a flat panel detector (that is, an area array), the detector 2 has a larger width. When the targets of the X-ray source 1 generate the X-rays merely for one cycle, the complete three-dimensional image of the inspected product 6 can be obtained.

Figure 2:
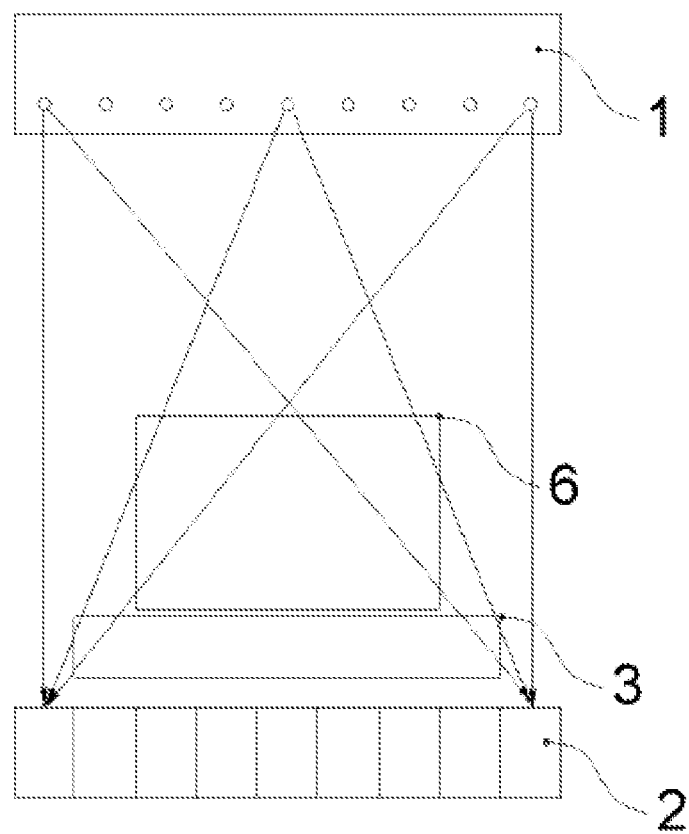
FIG. 2 shows a cross-sectional schematic diagram of an arrangement of an X-ray source and a detector of an X-ray product quality inspection device according to some embodiments of the present invention.

FIG. 2 shows a cross-sectional schematic diagram of an arrangement of the X-ray source and the detector of the X-ray product quality inspection device according to some embodiments of the present invention. As shown in FIG. 2, various targets of the X-ray source 1 are arranged in linear manner, and the X-ray source 1 is disposed above the transport device 3 (including the inspected product 6 positioned on the transport device 3). The distribution width (the size in the left-right direction in FIG. 2) of the plurality of targets is larger than the width of the inspected product 6. The detector 2 is in a linear array configuration, and arranged below the transport device 3. The row length (the size in the left-right direction in FIG. 2) of the detector array is also larger than the width of the inspected product 6. X-rays generated by each target of the X-ray source 1 penetrate through the inspected product 6, and then are received by the detector array. The transmission images with different views can be obtained. Moreover, the views have a large distribution range, and the multi-view image obtained finally has good multi-level information in the depth direction of the X-ray. Further, the present invention is not limited to above-described arrangement. Alternatively, and the variations of arrangement may be that the X-ray source 1 is arranged below the transport device 3 while the detector 2 is above the transport device 3, or that the X-ray source 1 is arranged on the left of the transport device 3 while the detector 2 is on the right, or that the X-ray source 1 is arranged on the right of the transport device 3 while the detector 2 is on the left, and so on, as long as the X-rays generated by the X-ray source 1 can irradiate the inspected product 6 and can be received by the detector 2.

Figure 3:
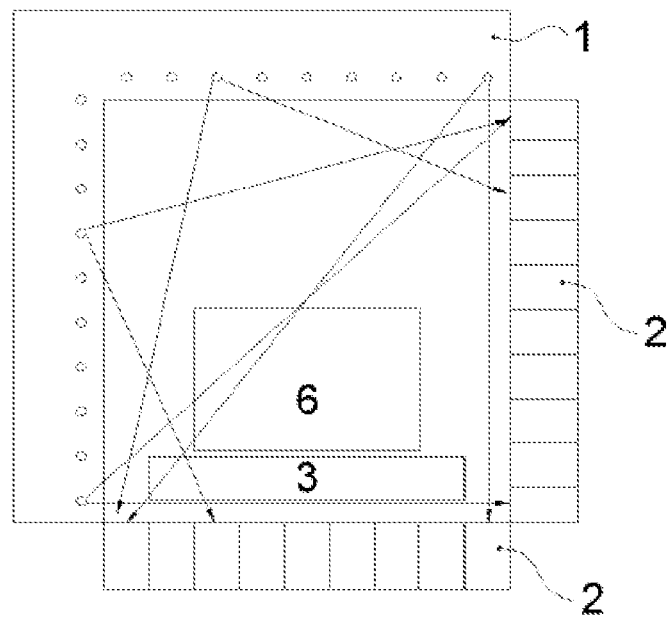
FIG. 3 shows a schematic diagram of an arrangement of an X-ray source and a detector which surrounds an inspected product according to some embodiments of the present invention.
Figure 4:
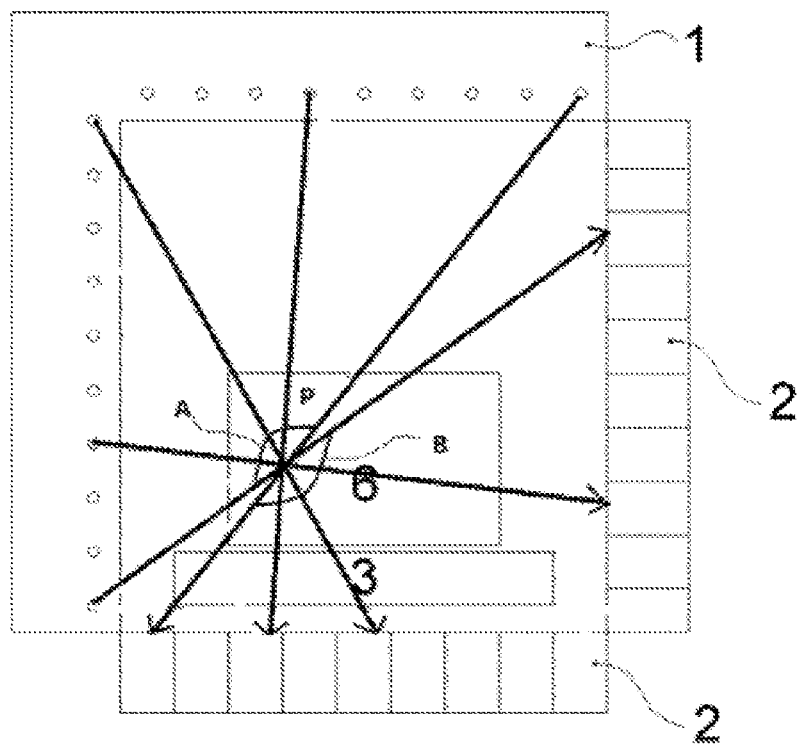
FIG. 4 shows a schematic diagram of field angles of X-rays from an X-ray source to any point of an inspected product and field angles of the X-rays from the point to a detector according to some embodiments of the present invention.

Further, FIG. 3 shows a schematic diagram of an arrangement according to some embodiments of the present invention, in which the X-ray source and the detector surround the inspected product. As shown in FIG. 3, the X-ray source 1 is in a shape of "L" which is formed by two straight line segments (correspondingly, the targets are also arranged in the shape of "L"). Further, the detector 2 is also in a shape of "L" formed by two straight line segments. The X-ray source 1 and the detector 2, in a joint way, completely surround the transport device 3 and the inspected product 6. For any point P on the inspected product 6, a sum of a field angle A of X-rays from the X-ray source 1 to the point P and a field angle B of X-rays from the point P to the detector 2 is larger than 180 degrees. The term "field angle" means an angle range of the X-ray passing the point P. Specifically, the field angle A of the X-rays from the X-ray source 1 to the point P means the angle range of the X-rays emitted from the X-ray source 1 before reaching the point P, which further can pass the point P and can be received by the detector 2, as shown in FIG. 4. The field angle B of X-rays from the point P to the detector 2 means the angle range of the X-rays which have passed the point P and can be received by the detector 2, as shown in FIG. 4. Also, the field angle B of the X-rays from the point P to the detector 2 can be not less than 90 degrees. Therefore, compared with the situation shown in FIG. 2, the situation shown in FIG. 3 and FIG. 4 has a larger view range, and can obtain many transmission images. A complete three-dimensional image of the inspected product 6 may be formed via reconstruction algorithms, and the structure and characteristics information of every location point on the inspected product 6 can be analyzed. This is a true "all-round" exhaustive inspection and analysis. Further, the arrangement of the X-ray source 1 and the detector 2 also may be in a shape of U, except for the shape L mentioned-above. Then, the variations of the arrangement also may adopt polyline with other angles, or combinations of more line segments. Alternatively, part of the X-ray source 1 or the entire X-ray source 1 can be changed into an arc shape, or part of the detector 2 or the entire detector 2 can be change into an arc shape.

Further, the power supply and control device 4 may further include an image analysis subsystem 44, which may include a storage device and an image analysis software. The storage device is used for storing standard images (or standard characteristic information) of the inspected product 6, making all the inspecting images of the inspected products 6 having been inspected automatically match the actual objects on numbers and storing them. The image analysis software is used to perform comparative analysis, for example, differential comparison, between the images generated by the image construction subsystem 43 for each inspected product 6 and the standard images (or the standard characteristic information), and according to set rules, to identify whether the inspected product 6 meets specific requirements, for example, whether there are quality defects (such as cracks, holes, trachoma, deformation, etc.), whether the processing (such as thickness, roughness, deformation, bending structure, stamping structure) is qualified, and whether the process (such as component assembly, welding spots, seams, joints, etc.) meets specific requirements. Further, the image analysis software is used for outputting the result of inspection and analysis on the inspected product 6 in a certain form (for example, alarm signal, control instructions, etc). The image analysis subsystem 44 also may not include a storage device, and the standard image of the inspected product 6 also may be stored in a storage device outside of the image analysis subsystem 44.

Further, the X-ray product quality inspection device of the present invention may further include a sorting device 5, which for example may be mounted on the transport device 3, and located downstream of the X-ray source 1 and the detector 2 in the moving direction of the inspected product 6. The sorting device 5 can sort the inspected products 6 according to magnitude of the signal from the detector 2 or the inspection and analysis result on the inspected product 6 supplied by the power supply and control device 4. That is, when the power supply and control device 4 determines that the signal from the detector 2 does not fall within a predetermined threshold range (that is, the inspected product 6 is unqualified), the sorting device 5 sorts out this unqualified product. Alternatively, the sorting device 5 sorts out the inspected product 6 in the case where the inspection and analysis result on the inspected product 6 supplied by the power supply and control device 4 indicates that the characteristic information of this inspected product 6 is inconsistent with the standard characteristic information. Alternatively, the sorting device 5 is controlled by the control subsystem 42, and sorts the inspected product 6 according to the image inspection and analysis result of the inspected product 6 given by the image analysis subsystem 44 (that is, the result of comparison between the image of the inspected product 6 formed by the image analysis subsystem 44 and the standard image). In addition, the sorting device 5 has a variety of embodiments. For example, the sorting device 5 may be embodied as a mechanical grip, which can grip out the unqualified inspected product 6 (or inspected product having other characteristics) and put it into an unqualified product basket (or other collecting devices), leaving qualified products continue to be operated on the product line. Further, the sorting device 5 can also be embodied as a pushing device (for example, air supplying device used in the process of inspecting drugs contained in medicine boxes or food contained in food packages) which is mounted on one side of the transport device 3, and has an opening or a movable door on the opposing side. The pushing device can operate in a pneumatic, electric, hydraulic or the like manner, push the unqualified inspected product 6 (or inspected product having other characteristics) on the transport device 3 out from the transport device 3 according to the instructions from the control system, leaving qualified products continue to be operated on the product line. Furthermore, the sorting device 5 can also be embodied as a path selection device. In this case, the transport device 3 has two separate paths in its downstream, and the path selection device is provided at the fork of these paths. The path selection device receives the instructions from the control subsystem, and when a qualified inspected product 6 comes, transfers it to a standard product line so that the qualified product continues to be operated. Meanwhile, when an unqualified inspected product 6 comes, the path selection device transfers the unqualified product to a defective product collecting line. Through the above-described sorting device or other sorting device which can achieve the same function, the products on the production line can be sorted according to the inspection and analysis result in the present invention.

Further, the X-ray product quality inspection device of the present invention may further include a shielding device 7, which is mounted on the outside of the X-ray source 1 and the detector 2 and encloses the X-ray inspecting region. The shielding device 7 is used to shield the X-rays in the non-application direction generated by the X-ray source 1 and to shield stray X-rays produced by the X-rays hitting on objects such as the inspected product 6, so that the radiation level around the X-ray product quality inspection device can reach a safe radiation level and comply with relevant national regulations, and also ensure workers at other positions of the production line to be protected from radiation. Generally, the shielding device 7 is made of heavy metal material, for example, lead, tungsten, etc. Sometimes, a certain amount of steel also may be used for convenience of processing. However, lead is preferable. Further, to enhance the shielding effect, the shielding device 7 generally encloses the transport device 3 and the inspected product 6, and extends for a certain distance along the transport device 3.

Further, the power supply and control device 4 can also include a display and operation subsystem 45, which is used to display the operating state of the X-ray product quality inspection device, to display the inspection image of the inspected product 6, and to display the inspection and analysis result. The display and operation subsystem 45 can also be used for inputting control instructions, providing human-machine interface, etc.

Figure 5:
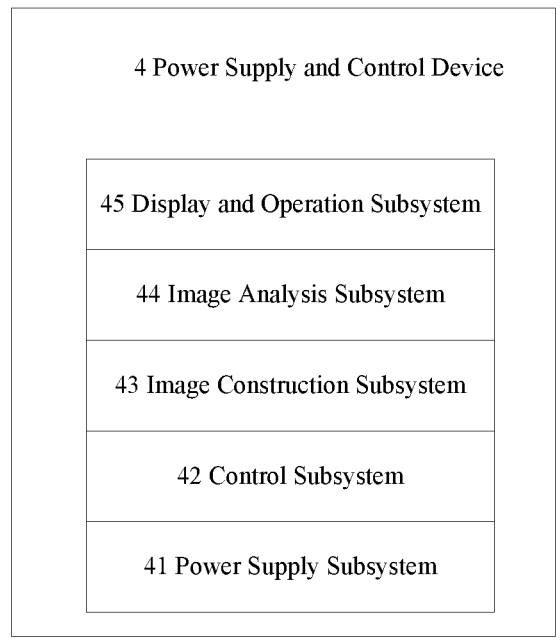
FIG. 5 shows a schematic diagram of a configuration of a power supply and control device according to some embodiments of the present invention.

FIG. 5 is a schematic diagram of a configuration of the power supply and control device 4. As shown in FIG. 5, the power supply and control device 4 functionally includes the power supply subsystem 41, the control subsystem 42, the image construction subsystem 43, the image analysis subsystem 44 and the display and operation system 45. The functions and roles of each subsystem are as described above. These subsystems may be structurally combined together as shown in FIG. 5, or can be configured as individual components separated from each other, as long as the functions and roles required by the present invention can be achieved.

It shall be particularly noted that, the X-ray source 1 of the present invention may be a multiple-energy X-ray source, for example, dual-energy X-ray source. X-rays of different energies may be obtained by for example setting different target materials at different target positions of the X-ray source 1. The target materials of the X-ray source typically comprise tungsten, molybdenum, gold, copper, and so on. Since different materials have different spectral characteristics, and therefore X-rays generated by different target materials at the same anode voltage have different characteristic peaks, i.e. different energies. X-rays of different energies also can be generated by applying different anodic high voltages to the anode at different cycles during which X-ray is generated (in the case where the X-ray source has multiple targets, the cycle is defined as a time period during which each target generates X-ray for one time). The employ of the multiple-energy X-ray source improves the image quality of the X-ray product quality inspection device, for example, adding the function of identifying physical materials or other functions.

It shall be particularly noted that, the detector 2 of the present invention may be a dual-energy detector assembly. That is, for each location point, the assembly contains both a low-energy detector which is sensitive to the X-ray of low energy and a high-energy detector which is sensitive to the X-ray of high energy. The detector group can obtain a high-energy image and a low-energy image at the same time, when the X-ray source generates X-rays each time. It is possible to obtain more information, and to improve the quality of the final detection image of the inspected product.

According to the above-described contents of the description in this application, as a specific embodiment, the embodiment 1 can provide an X-ray product quality online inspection device, which comprises: a distributed X-ray source having a plurality of targets, wherein the distributed X-ray source can generate X-rays for radiating an inspected product from the plurality of targets in a predetermined sequence; a detector for receiving the X-rays generated by the distributed X-ray source; a transporting device for carrying the inspected product to pass through a X-ray radiation region; a power supply and control device for supplying power to the X-ray product quality online inspection device and controlling it, wherein the power supply and control device forms characteristic information of the inspected product according to a signal from the detector, and then provides an inspection and analysis result of the inspected product according to the characteristic information.

The X-ray product quality online inspection device according to the embodiment 1 can inspect the products in the production site flexibly. For example, an inspection site can be specially provided to place the X-ray product quality online inspection device of the present invention, and the products unloaded from the production lines can be transferred to this special inspection site. The workers can sort out the unqualified products in situ according to the inspection and analysis result of the products, so as to facilitate subsequent processing of the products. Further, the X-ray product quality online inspection device is not fixedly connected with certain production line, and thus can be used in common for a plurality of production lines. Therefore, the inspection cost and space for inspecting site are saved. Further, the X-ray product quality online inspection device of the present invention can also be connected with a plurality of production lines at the same time. For example, a collection device can be used to connect the ends of the plurality of production lines to the X-ray product quality online inspection device at the same time, and thus the process of transferring the products to the inspecting site is omitted.

Furthermore, the X-ray product quality online inspection device of the present invention can also have a sorting device, which is located downstream of the distributed X-ray source and the detector in the moving direction of the inspected product, and is used to sort the inspected products according to the signal from the detector or the inspection and analysis result from the power supply and control device under the control of the power supply and control device. Therefore, a mechanical and automatic sorting is achieved and thus the human cost for manual sorting is saved. Of course, manual judging the above-mentioned inspection and analysis result and manual sorting also fall within the protective scope of the present invention.

Further, according to the contents of the description, various combinations or modifications can be made to the configuration of the above-described embodiment 1, and the modified technical solutions also fall within the protective scope of the present invention.

One embodiment of the present invention is described as above. However, the present invention is not limited to this, and the present invention also comprises the following specific embodiment, that is, embodiment 2.

The embodiment 2 provides an X-ray product quality online inspection device, in which the structure of various components and operation principles are the same as the embodiment 1, except for the transport device 3. That is, in the embodiment 2, the transport device 3 is located between the X-ray source 1 and the detector 2 for carrying the inspected product 6 to pass through the X-ray radiation region, and is arranged as a continuous transport mechanism which matches the production line of the inspected products 6.

In the embodiment 2, the transport device 3 is arranged as a continuous transport mechanism which matches the production line of the inspected products 6. This means that: (A) the transportation capacity of the transport device 3 matches that of the production line (that is, all the inspected products 6 produced within a unit time on the production line are carried by the transport device 3 to pass through the X-ray product quality online inspection device by which the inspection is completed and the characteristic information is obtained, without overstocking of product); and (B) the movement of the inspected products 6 from the production line to the transport device 3, and from the transport device 3 to the production line is continuous, without pause, waiting, halfway handling and other processes. There are various specific implementations. For example, (1) the transport device 3 itself may be a section of the production line; (2) the transport device 3 may be a part interposed into the production line, which has the same width and moving speed as the production line; (3) the transport device 3 may be a part interposed into the production line, which has a larger width but a lower moving speed and can transport the same amount of products per unit time as compared to the production line; (4) the transport device 3 may be a part interposed into the production line, which has a smaller width but a higher moving speed and can transport the same amount of products per unit time as compared to the production line; and (5) the transport device 3 may be a part interposed into the production line, which has a same width, a higher moving speed and a larger product pitch and can transport the same amount of products per unit time as compared to the production line. Further, besides the above-mentioned implementations (1)~(5), other implementations also can be used, as long as the production inspection of the products on the production line can be completed.

The workers can perform analysis on the inspected product 6 according to the characteristic information of the inspected product 6 formed by the power supply and control device 4, and determines for example, whether the product is qualified. Furthermore, the power supply and control device 4 can also include a characteristic analyzing module, which is able to perform for example threshold comparison of signal, differential comparison of image, and so on. For example, the characteristic analyzing module automatically provides the inspection and analysis result of the inspected product 6 (for example, whether the product is qualified, etc.) by comparison and analysis according to the above-mentioned characteristic information of the inspected product 6.

The workers can sort the inspected products 6, for example, sorting out the unqualified products, according to the analyzing result of the inspected products 6 provided by the power supply and control device 4. Furthermore, the X-ray product quality online inspection device of the embodiment 2 also can include a sorting device 5, which is mounted on the transport device 3 or is arranges in a same manner as in the embodiment 1. The sorting device 5 is controlled by the power supply and control device 4, and can automatically sort the inspected product 6 on the transport device 3, for example gripping out, pushing out, diverting out the products having some characteristics, according to the analyzing result of the inspected product 6 provided by the power supply and control device 4. Here, the sorting device 5 also can use the sorting device described in the embodiment 1.

Further, the X-ray product quality online inspection device of the embodiment 2 also can has a shielding device as the embodiment 1, and the structural configuration of the distributed X-ray source, the detectors, etc also can be the same as that of the embodiment 1.

The X-ray product quality online inspection device according to the embodiment 2 can achieve the online inspection to products. As such, it is possible to start sorting the products once they are unloaded from the production line, or it is possible that the products are directly sorted by the workers immediately after the online inspection.

Further, according to the contents of the description, various combinations or modifications can be made to the configuration of the above-described embodiment 2, and the modified technical solutions also fall within the protective scope of the present invention.

The X-ray product quality inspection device of the present invention can achieve an all-round inspection to products on factory production lines, automatically analyze inspection images, and automatically sort products on the production lines according to the analysis result. The present invention can operate flexibly, has strong adaptability for different products, can inspect products roundly and exhaustively, and has a high degree of automation. Thus, the present invention can significantly increase production efficiency and reduce production costs.

The present invention is not limited to the contents described as above and also can make various combinations and modifications to the X-ray product quality inspection device as described above.

As described above, the present invention is illustrated, but not limited to this. It shall be understood that, the present invention can make various modifications within the spirit of the invention.

REFERENCE SIGN LIST

1 X-ray Source
2 Detector
3 Transport Device
4 Power Supply and Control Device
5 Sorting Device
6 Inspected Product
7 Shielding Device
41 Power Supply Subsystem
42 Control Subsystem
43 Image Construction Subsystem
44 Image Analysis Subsystem
45 Display and Operation Subsystem

What is claimed is:

1. An X-ray product quality online inspection device, comprising:
  a distributed X-ray source having a plurality of targets, wherein the distributed X-ray source is able to generate X-rays for irradiating an inspected product from the plurality of targets in a predetermined sequence;
  a detector for receiving the X-rays generated by the distributed X-ray source and outputting a signal representing characteristics of the received X-rays;
  a transport device which is located between the distributed X-ray source and the detector for carrying the inspected product to pass through an X-ray radiation region, wherein the transport device is arranged as a continuous transport mechanism which matches a production line for the inspected product; and
  a power supply and control device, which is used to supply power to and control the X-ray product quality online inspection device,
  wherein the detector is arranged in a form of a detector array and number of rows of the detector array is set based on a moving speed of the inspected product carried by the transport device, and amount of the inspected products per unit time transported by the transport device is the same as amount of the inspected products transported by the production line,
  wherein the power supply and control device further forms characteristic information of the inspected product according to the signal from the detector, and provides an inspection and analysis result of the inspected product according to the characteristic information, and
  wherein the X-ray product quality online inspection device further comprises a sorting device, which is located downstream of the distributed X-ray source and the detector in a moving direction of the inspected product, and is used to sort the inspected product according to the inspection and analysis result from the power supply and control device, under the control of the power supply and control device.

2. The X-ray product quality online inspection device according to claim 1, wherein the power supply and control means determines whether the signal from the detector falls within a predetermined threshold range, and the sorting means sorts out the inspected product when it is determined that the signal from the detector does not fall within the threshold range.

3. The X-ray product quality online inspection device according to claim 1, wherein the sorting means sorts out the inspected product in a case where the inspection and analysis result from the power supply and control means indicates that the characteristic information of the inspected product is inconsistent with standard characteristic information.

4. The X-ray product quality online inspection device according to claim 1, wherein the power supply and control means further comprises an image construction subsystem, which is used to receive the signal from the detector and to form a multi-view image or a three-dimensional image expressing the characteristic information of the inspected product.

5. The X-ray product quality online inspection device according to claim 4, wherein:
  the power supply and control means further comprises an image analysis subsystem, which is used to compare and analyze the inspected image obtained by the image construction subsystem and an image of a standard product according to a predetermined rule, and
  the inspected product is sorted according to the comparison and analysis result of the image analysis subsystem.

6. The X-ray product quality online inspection device according to claim 5, wherein the power supply and control means further comprises a display and operation subsystem for displaying at least one of: operating state of the X-ray product quality online inspection device, an inspection image of the inspected product, the inspection and analysis result, and inputting of control instructions.

7. The X-ray product quality online inspection device according to claim 1 further comprising:
  a shielding structure, which encloses the X-ray radiation region and shields stray X-rays.

8. The X-ray product quality online inspection device according to claim 7, wherein the shield structure comprises lead or tungsten.

9. The X-ray product quality online inspection device according to claim 1 wherein all the inspected products produced on the production line per unit time can be carried by the transport device to continuously pass through the X-ray product quality online inspection device within a unit time to finish the inspection.

10. The X-ray product quality online inspection device according to claim 9, wherein the transport device itself is a part of a factory production line.

11. The X-ray product quality online inspection device according to claim 1 wherein the plurality of targets of the distributed X-ray source are arranged in straight line, polyline, arc or the combination thereof.

12. The X-ray product quality online inspection device according to claim 1, wherein an arrangement direction of the plurality of targets of the distributed X-ray source is perpendicular to the moving direction of the inspected product.

13. The X-ray product quality online inspection device according to claim 1, wherein the detector is one of a flat panel detector having numerous detection units, a detector having a plurality of detection units in a one-dimensional linear array, and a detector having a plurality of detection units in a two-dimensional matrix array, and is able to receive the X-rays at a plurality of positions at the same time.

14. The X-ray product quality online inspection device according to claim 1, wherein a sum of a field angle of the X-rays from the distributed X-ray source to any point on the inspected product and a field angle of the X-rays from the point to the detector is more than 180 degrees.

15. The X-ray product quality online inspection device according to claim 1, wherein the distributed X-ray source is a dual-energy X-ray source.

16. The X-ray product quality online inspection device according to claim 1, wherein a time period during which the plurality of targets at different positions of the distributed X-ray source sequentially emits the X-rays is at a level of microsecond.

17. The X-ray product quality online inspection device according to claim 1, wherein the plurality of targets of the distributed X-ray source are arranged in an arc shape or a spiral shape along the moving direction of the inspected product.

18. The X-ray product quality online inspection device according to claim 1, wherein the detector is a dual-energy detector.

19. The X-ray product quality online inspection device according to claim 1, wherein the sorting device is mounted to the transport device.

20. The X-ray product quality online inspection device according to claim 1, wherein the sorting device is selected from the group consisting of a mechanical grip, a pushing device, and a path selection device.

* * * * *